United States Patent [19]

Walton

[11] Patent Number: 5,264,511
[45] Date of Patent: Nov. 23, 1993

[54] POLYMERS OF BIS (ETHYNYLSTYRYL) BENZENE AND RELATED MONOMERS

[75] Inventor: Theordore R. Walton, Annandale, Va.

[73] Assignee: The United States of America as represented by the Secretary of the Navy, Washington, D.C.

[21] Appl. No.: 906,344

[22] Filed: Jun. 30, 1992

[51] Int. Cl.$^5$ .................. C08F 38/00; C07C 43/205; C07C 15/52

[52] U.S. Cl. ................................ 526/285; 526/247; 526/248; 526/251; 528/481; 528/503; 568/583; 568/585; 568/631; 568/635; 568/646; 568/647; 568/659; 568/660; 568/661; 568/928; 570/182; 570/200; 585/25; 585/436; 585/505

[58] Field of Search ............... 526/285, 247, 248, 251; 528/481; 585/25, 505, 436; 568/583, 585, 631, 635, 646, 647, 659, 660, 661, 928; 570/182, 200

[56] References Cited

U.S. PATENT DOCUMENTS

| | | | |
|---|---|---|---|
| 3,756,982 | 9/1973 | Korshak et al. | 526/285 X |
| 4,336,362 | 6/1982 | Walton | 526/248 |
| 4,417,039 | 11/1983 | Reinhardt et al. | 526/285 |
| 4,547,592 | 10/1985 | Reinhardt et al. | 526/285 X |
| 4,730,032 | 3/1988 | Rossi et al. | 526/285 |

FOREIGN PATENT DOCUMENTS

| | | | |
|---|---|---|---|
| 59-89310 | 5/1984 | Japan | 526/285 |
| 60-86106 | 5/1985 | Japan | 526/285 |

*Primary Examiner*—Fred Teskin
*Attorney, Agent, or Firm*—Thomas E. McDonnell; George A. Kap

[57] ABSTRACT

Monomers, B-stage polymers, C-stage polymers, cured polymers and electrically conducting polymers of acetylene-terminated aromatic monomers containing three benzene rings separated by ethylene groups are disclosed. These new polymers can withstand aggressive environments and are particularly adapted for use in high temperature composites in addition to the utilization of their electrical conducting properties. Preparation of these materials is accomplished by melt polymerization and heat treatment at high temperatures.

20 Claims, No Drawings

POLYMERS OF BIS (ETHYNYLSTYRYL) BENZENE AND RELATED MONOMERS

FIELD OF INVENTION

This invention relates to monomers and to polymers which can be used in certain structural applications. More specifically, this invention relates to cured polymers which are electrically conducting and which are resistant to high temperatures and/or aggressive environment.

BACKGROUND OF INVENTION

Most all organic polymers are non-conductive. Electrical conductivity can be introduced into these non-conductive materials by adding conductive fillers such as metal or carbon powders. Typically, only low loading of the conductive filler can be used before polymer properties begin to deteriorate. Further, it is difficult to control the exact conductivity of the final product because the material passes from the insulating state to maximum conductivity over a very narrow range of filler content.

A newer approach to conductive organic polymers involves the addition of a more or less reactive species, i.e., a dopant, to a conjugated or unsaturated polymer to oxidize or reduce it to the conductive state. This approach, however, leaves either negative or positive charges on the polymer which compromises the environmental stability of the system. Although a few of these doped polymers are stable in an ambient environment, most doped systems must be protected from the air, moisture and elevated temperatures or they rapidly lose their conductivity. Even the more stable doped polymers will lose their conductivity on exposure to more aggressive environments.

U.S. Pat. No. 4,336,362 to Walton discloses acetylene-terminated dianil monomers which are polymerized at a temperature below 150° C. or, more specifically, in the range of about 130°-140° C., cured preferably in steps from about 150° C. to about 300°, and postcured preferably in steps from about 400° to 600° C. These polymers, after postcure, are electrically conducting and can withstand high temperatures and wet environments. U.S. Pat. No. 4,116,945 to Griffith et al discloses bisphthalonitrile polymers which can be processed by conventional resin technology and which are electrically conducting.

SUMMARY OF INVENTION

An object of this invention is electrically conducting polymers which have thermal and environmental stability.

Another object of this invention is the electrically conducting polymers which do not contain electrically conducting metal powders.

Another object of this invention is monomers, B-stage polymers, and polymers of bis(ethynylstyryl)benzenes.

Another object of this invention is polymers which are not electrically conducting when polymerized at a lower temperature but which become electrically conducting after processing same at a higher temperature.

Another object of this invention is B-stage polymers of bis(ethynylstyryl)benzenes which can be melted at a lower temperature and then heated at a higher temperature to polymerize same and then further heated at still higher temperature to render same electrically conducting.

Another object of this invention is the preparation of thermally stable polymers of bis(ethynylstyryl)benzenes.

These and other objectives of this invention are achieved by a three-dimensional network polymerization of bis(ethynylstyryl)benzenes which become electrically conducting on further processing at an elevated temperature.

DETAILED DESCRIPTION OF INVENTION

This invention pertains to monomers, B-stage polymers, polymers, and to preparation thereof. More specifically, this invention pertains to bis(ethynylstyryl)benzene monomers, B-stage polymers, and polymers therefrom in cured and uncured state which are not electrically conducting but by further processing at higher temperatures become electrically conducting.

The bis(ethynylstyryl)benzene monomers are characterized by the following structure, which are all carbon/hydrogen in their unsubstituted form:

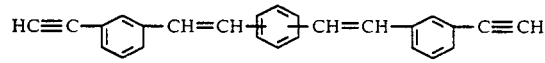

The above structure, which represents one molecule, is characterized by a terminal acetylenic group attached at each end thereof to a phenyl group and a pair of alkylene or ethylene groups each attached at both ends to phenyl groups with the result that the central phenyl group is situated between the two ethylene groups. In the above structure, there is one phenyl group between each acetylenic group and each ethylene group. There is a total of three phenyl groups per molecule, as depicted above, and each phenyl group is bonded to two different groups at different positions on the phenyl ring. The structure shown above can be unsubstituted or the hydrogens thereon can be substituted with a desired substituent. Suitable substituents include phenyl groups, halogens, alkyl groups, nitro groups, alkoxy groups, phenoxy groups, ether groups, and the like. Preferred halogens are fluorine, chlorine and bromine; preferred alkyl groups contain 1–20 carbon atoms; especially 1–6, preferred phenoxy groups contain 6–9 carbon atoms; preferred alkoxy groups contain 1–6 carbon atoms; and preferred ether groups contain 1–6 carbon atoms. Substitution on the benzene rings is more likely than for the hydrogen atoms on the acetylene or the ethylene moieties.

The 1,3-bis(ethynylstyryl)benzene (II) monomer, i.e., the 1,3-isomer, was prepared in the manner outlined below, with the Roman numerals referring to the reaction compounds:

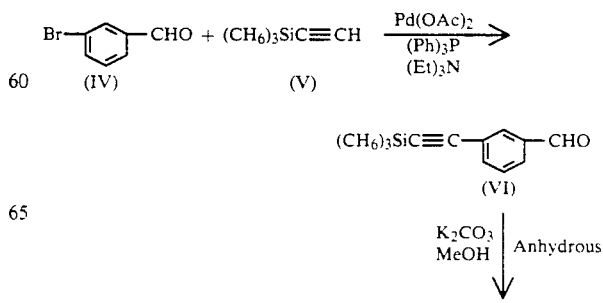

-continued

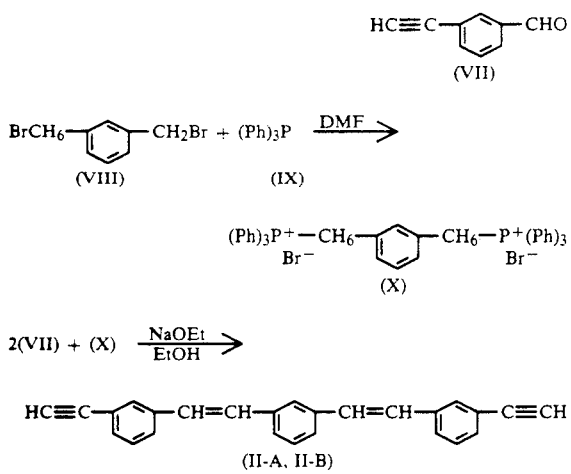

Pursuant to the procedure summarized above, a 500 mL, three-neck flask was fitted with a nitrogen inlet tube, a 125 mL dropping funnel, thermometer, a condenser open to the atmosphere, and a magnetic stirrer. The system was flushed with nitrogen, and this atmosphere was kept over the solution during the reaction. The dried bis-phosphonium salt (X) in amount of 9.09 g or $1.15 \times 10^{-2}$ mol, the ethynylbenzaldehyde (VII) in amount of 3.30 g or $2.54 \times 10^{-2}$ mol with 10% excess, and 150 mL anhydrous ethyl alcohol were placed in the flask, Sodium metal in amount of 0.64 g or $2.78 \times 10^{-2}$ mol was slowly added to 125 mL of anhydrous ethyl alcohol in the dropping funnel. After all sodium had dissolved, stirring was started and 50 mL of the EtOH-NaOEt solution was added rapidly over a 1 minute period. After the remaining NaOEt-EtOH solution was added dropwise over 15 minutes, stirring was continued at room temperature for 2 hours. The reaction was followed by IR by observing the disappearance of the aldehyde absorption at 1698 cm$^{-1}$, a shift in the C≡C absorption from 3255 cm$^{-1}$ in the aldehyde to 3290 cm$^{-1}$ in the product, and the appearance of triphenylphosphine oxide.

The bis-styrylbenzenes can exist in three isometric forms, i.e., trans-trans, cis-cis, and trans-cis forms. Two products i.e., II-A and II-B, were isolated from the reaction that corresponded to Structure II. They differ by the relative amounts of cis and trans structures present. The initial product II-A was precipitated by addition of 150 mL of water to the reaction mixture, isolated by filtration, and washed with 2:1 EtOH-H$_2$O solution. A second viscous, liquid product, i.e., impure II-B, was recovered from the filtrate by careful refiltration and isolated by dissolving in methylene chloride and final removal of solvent.

The initially isolated soft, solid product II-A, in 41% yield, was reasonably pure by IR, NMR, and carbon/hydrogen analysis. The viscous liquid product II-B was contaminated with triphenyphosphine oxide, a by-product from the reaction. By passing a solution of this material in toluene through an acidic alumina (Al$_2$O$_3$) column, the triphenylphosphine oxide was completely removed and a yield of 40% of theory was obtained. The total yield of solid and liquid phases, or II-A and II-B, was 81%. Two melting phases of the II-A isomer high in trans configuration were observed: solid to cloudy liquid at about 40° C. and cloudy liquid to clear liquid at about 120° C. The II-B isomer high in cis configuration was a viscous liquid at room temperature.

Pure single geometric isomers were not isolated. Two fractions were obtained: a soft solid II-A that is higher in trans configuration and a viscous liquid II-B that is higher in cis configuration. Since there are two double bonds present, these mixtures may consist of the trans-trans and/or trans-cis and/or cis-cis structures. The IR absorption spectra are qualitatively the same for both mixtures when both are run as liquid films, but some absorption intensities are different. For example, as might be expected, II-A has a stronger absorbance at 960 cm$^{-1}$ than does II-B (trans absorption). Based on calculations and/or evaluations made, tentative values are 65% trans and 35% cis distribution for the solid product II-A, and 37% trans and 63% cis distribution for the liquid product II-B.

The 1,3-isomers are in a homogeneous liquid state at least 30° C. below the cure temperature and they have a good processing window, that is, the melts can be held at about 120°-125° C. for several hours without a significant change in viscosity.

The procedure for preparing 1,4-bis(3-ethynylstyryl)-benzene (III), or the 1,4-isomer, was essentially as described for the 1,3-isomer except that the bis-triphenylphosphonium salt of alpha, alpha-dibromo-p-xylene was used. Pursuant to this procedure, into a 1 L flask equipped with a magnetic stirrer, Claisen adaptor, pressure-equalizing dropping funnel, and nitrogen inlet, 6.00 g or $4.61 \times 10^{-2}$ mol of 3-ethynylbenzaldehyde, 18.18 g or $2.31 \times 10^{-2}$ mol of the dried phosphonium salt, and 30 mL of anhydrous ethyl alcohol were placed. Not all the materials dissolved and a slurry was formed. Another 250 mL of anhydrous ethyl alcohol was placed in the dropping funnel and 1.08 g or $4.70 \times 10^{-2}$ mol of sodium metal was added over a 30 minute period. Approximately 100 mL of the EtOH-NaOEt solution was added rapidly over 1-2 minutes to the stirred reaction mixture under a nitrogen atmosphere and then the remainder was added dropwise over about 15 minutes; little or no heat was produced during the addition. The reaction mixture was stirred at room temperature for 6 hours during which time, chunks of the salt were manually broken up in the reaction flask. The reaction was terminated by addition of 200 mL water. The product (III) was isolated and purified by filtration of the refrigerated cooled solution, recrystallization from benzene, and vacuum drying at 50° C. Yield was 0.72 g or 9.4%, and melting point was 183°-185° C. Only the all-trans-trans isomer was obtained in this preparation. It is not known why the overall yield was so low, but a repeat of this same procedure gave similar results. Because the processing window, i.e., melting point vs. temperature of cure, was so narrow, the 1,4-isomer did not appear to be a practical material for melt polymerization technique.

The 1,4-isomer was isolated in the pure trans-trans form as indicated by a reasonably sharp melting point and a very strong absorption at 968 cm$^{-1}$ in the IR (trans absorption). The presence of a chemical shift at 7.11 ppm in the proton NMR appears to be indicative of a trans configuration, and the lack of any absorption between 7 and 6.5 ppm appears to be indicative of the absence of a cis configuration for this system.

The monomers disclosed herein can be polymerized and then postcured or thermally processed in an inert atmosphere to develop certain of their properties, such as electrical conductivity. Onset of polymerization can be detected by monitoring viscosity of the monomer melt. Viscosity of the melt will increase as polymerization proceeds and at a point during polymerization, the melt gels which is indicative of polymerization in progress. The 1,3-isomers, for instance, will gel in 1 hour at 150° C. The 1,3-isomers include the soft or amorphous solid cis/trans isomer mixture II-A and/or the liquid cis/trans isomer mixture II-B. Polymerization can be stopped at a B-stage and the product, i.e., B-stage polymer, can be cooled and stored for later use. At this stage, the product is a frangible solid.

The advantage of using a B-stage polymer resides in the lower temperature at which the B-stage polymer melts and thus the lower temperature at which the material can be utilized. The B-stage polymer is obtained by heating the monomer and continuing to heat the monomer until the viscosity of the melt begins to increase due to the onset of polymerization, which is termed the B-stage. To obtain the C-stage, the B-stage polymer is melted and heated at a temperature from about 140° C. to about 300° C. The B-stage polymer is not fully polymerized and is an insulator, as is the C-stage polymer, i.e., it does not have electrical conductivity.

Polymerization to C-stage polymer can commence with a monomer or a B-stage polymer. Polymerization is accompanied by increase in viscosity of the melt while the melt is heated. Generally, polymerization reaction will be conducted over a temperature range of 100°–300° C. for a period of up to 10 hours, preferably at 120°–250° C. for a period of about 1 minute to 1 hour. Polymerization of the herein disclosed monomers or B-stage polymers is also accompanied by disappearance of the acetylene groups, as can be followed by infrared analysis. In addition to showing increasing viscosity during polymerization, DSC curves should show a very strong exotherm peaking at 210°–230° C. The 1,3-isomers should initially be polymerized at 130° to 150° C. in 1 to 3 hours, preferably at 140° C. in 2 hours. Because the polymerization exotherm (55–65 Kcal/mole) is so energetic, it is desirable to initiate the polymerization at the lower temperature to prevent a "run-away" reaction during the polymerization of the acetylene groups. Once most of the acetylene groups have reacted, the polymerization can be completed at higher temperatures of up to 300° C. If initial polymerization is attempted at higher temperatures, for example, 180°–200° C., the reaction becomes so violent because of the high heat of reaction that the polymerizing material is decomposed to a charred, porous mass and polymeric properties destroyed. As already pointed out, the 1,3-isomers have good processing window, however, the 1,4-isomer does not present a very practical system for melt polymerization because rapid cure at the melting point provides little or no time for processing in the liquid phase. The B-stage polymer and the final polymer product or C-stage polymer are thermoplastic insulators.

The polymerization occurs at the acetylene groups which initially form polyene or conjugated structures. The resulting polymer is a completely conjugated, three-dimensional network polymer.

The purpose of the cure is to develop properties of a polymer. The cure promotes crosslinking in a polymer chain and between different polymer chains forming a three-dimensional network polymer which is insoluble in the ordinary solvents. Final curing temperature should be in excess of polymerization exotherm temperature(maximum of about 210°–230° C. by DSC) and below decomposition temperature of the polymer. Curing of the polymers described herein can be accomplished at a temperature of 130°–400° C. for a time of 1 minute to 50 hours, preferably at 150°–300° C. for a time of 10 minutes to 20 hours. Although the suggested curing temperature range is broad and a time period that may appear long, the polymers disclosed herein can be cured in about 5 hours at about 300° C. after initial cure at 130°–150° C. for a couple of hours. After initial cure at 300° C. for a period of 5 hours, the cured polymers are thermosetting, nonconducting, hard black solids that assume the shape of the container in which they are cured. Also, after about 5 hours at about 300° C., all acetylene groups should be reacted and infrared analysis should not show any acetylene absorption.

With respect to the specific polymers disclosed herein, the cis/trans-1,3-isomer mixtures II-A and II-B were initially cured in either a glass vial in an oil bath or in an aluminum planchet on a hot plate starting at 130° C. Over a period of 1.5 hours, the temperature was gradually increased to 150° C. and held there for 1 hour. The gelled samples were then immediately transferred to a furnace preheated to 150° C. and held there for 1 additional hour. The temperature was increased to 200° C. for 1 hour, then 250° C. for 1 hour, and finally to 300° C. for 50 hours.

The all-trans-1,4-isomer (III) had to be cured by a different approach because it melts substantially above the temperature where the cure is initiated. It was necessary to rapidly heat the powder sample to 190°–200° C. to melt it quickly before it cured into an infusible, powdery mass in the solid state. Although this procedure is necessary to obtain a cured material for evaluation, it has the problem that the reaction can become uncontrolled, resulting in substantial decomposition and weight loss because of the high energetic exotherm of the reacting acetylene groups at this temperature. The initial cure of these acetylene-terminated resins (III) should be controlled below 150°–160° C. Obviously, with this 1,4-isomer, melt polymerization is not possible with more gentle cure. By keeping the sample small, it was possible to obtain a cured sample for evaluation. The sample was of poor quality in that it contained a number of pinpoint-head-size voids throughout. Indeed, the 1.5% weight loss observed during the cure of the sample for 50 hours at 300° C. indicated that the sample may have undergone some decomposition that is not observed when the normal cure procedure is followed.

After the final cure for 5–50 hours at 300° C. in air, the materials are nonconducting, hard, black solids that assume the shape of the container in which they were cured. To make the materials conductive, their conjugated network must be extended by postcuring or processing them at higher temperatures in an inert atmosphere. During this processing, it is believed that the initial polyene structures formed during the polymerization of the acetylene groups are converted into aromatic or condensed aromatic ring structures. To develop electrical conductivity, the polymers must be heat-treated at a temperature in excess of about 400° C. in an inert atmosphere such as nitrogen, argon, or vacuum. The time-temperature profile depends on the final conductivity desired. In a preferred embodiment, heating should be at 400°–1200° C. for duration of 1–500 hours, especially at 500°–700° C. for duration of 5–200 hours. During the heat treatment, although some weight loss and some shrinkage does occur, the material or the polymer maintains its integrity and its strength improves. Heating and cooling rates were 0.5° C. per minute, and samples were held at the specific temperature for 100 hours, or as otherwise indicated. The weight loss and conductivity for the three materials described herein i.e., II-A, II-B, and III, are summarized in Table I, below:

TABLE I

| Post-Processing Conditions[a] | | II-B 1,3-Bis(3-ethynylstyryl)-benzene (cis rich) | | II-A 1,3-Bis(3-ethynylstyryl)-benzene (trans rich) | | III 1,4-Bis(3-ethynylstyryl)-benzene (all trans) | |
|---|---|---|---|---|---|---|---|
| Temp (°C.) | Time (h) | % Wt loss | Cond (s/cm) | % Wt loss | Cond (s/cm) | % Wt loss | Cond (s/cm) |
| 400 | 100 | 3.49 | b | 3.50 | b | 7.87 | b |
| 500 | 100 | 9.09 | b | 11.37 | b | 14.26 | b |
| 600 | 100 | 12.08 | $3.93 \times 10^{-2}$ | 16.18 | $2.40 \times 10^{-1}$ | 18.75 | $1.60 \times 10^{-1}$ |
| 700 | 100 | 14.32 | $1.46 \times 10^{1}$ | 19.09 | $2.11 \times 10^{1}$ | 21.57 | $1.72 \times 10^{1}$ |
| 900 | 5 | | | 20.66 | $9.30 \times 10^{1}$ | 24.89 | $5.00 \times 10^{1}$ |
| 1200 | 5 | | | 23.40 | $1.76 \times 10^{2}$ | 31.85 | $9.85 \times 10^{1}$ |

[a]Heating and cooling rates were 0.5° C./min; argon atmosphere.
b Conductivity too low to measure on four-point probe; minimum conductivity that could be measured with out set up was $10^{-8}$ to $10^{-7}$ s/cm.

The weight losses reported in Table I are for the cumulative weight loss from the initial cure. For example, the weight loss at 600° C. includes the weight loss for 100 hours at 600° C., 100 hours at 500° C., and 100 hours at 400° C. At such temperatures in inert atmospheres, it is expected that most other known polymeric materials would be degraded by more than 50% by weight. At high temperatures it is believed that nitrogen would be eliminated from the polymer before carbon and that is why an all carbon-hydrogen polymers are expected to do better than polymers that contain other hetero atoms disclosed in U.S. Pat. No. 4,116,945 and U.S. Pat. No. 4,336,362.

In addition to the TGA studies, the weight losses reported in Table I for the long processing times at the high temperatures are indicative of the overall high thermal stability of these acetylene-terminated resins.

The data in Table I shows that heating a polymer prepared from II-B at 700° C. for 100 hours, yielded a conductivity of 14.6 siemens per centimeter (s/cm) or (ohms-cm)$^{-1}$. Corresponding cumulative weight loss of the polymer II-B sample was 14.32 weight percent. For purpose of orientation, copper has conductivity of about $10^5$–$10^6$ s/cm. The data in Table I also supports the proposition that all the herein disclosed polymers can attain conductivity of at least about $10^{-10}$ s/cm to about $10^2$ which remains substantially constant after exposing the polymer to boiling water for 1000 hours.

The polymers disclosed herein have high environmental stability. For example, a conducting polymer prepared from the cis-rich monomer II-B (conductivity 10 s/cm) was compared to one of the more stable "doped" conducting polymers (100s/cm), an arylsulfonate-doped polypyrrole, in a boiling water test. The polymer from fraction II-B showed no change in conductivity during the 1000 hours in boiling water while the doped polypyrrole very rapidly lost its conductivity. After 100 hours, conductivity of polypyrrole could no longer be measured by the four-point technique because it was less than $10^{-8}$ s/cm.

Once these materials have been processed to high temperature to introduce conductivity, they can be aged at lower temperatures without further change in the room temperature conductivity. For example, after samples prepared from the all-carbon-hydrogen 1,3-isomers from fractions II-A and II-B have been processed to 700° C for 100 hours to give conductivities of 14 to 21 s/cm, no change in this room-temperature conductivity was observed when they were aged for over 500 hours at 500° C. in an inert atmosphere; they also do not show any weight change. The doped polypyrrole was destroyed under these same conditions.

The new materials combine high thermal and environmental stability and electrical conductivity without the necessity of adding conductive additives. The cure is easily carried out by melt polymerization without the need for adding a curing agent or a coreactant. Furthermore, electrical conductivity is not degraded by exposing the material to aggressive environments, such as boiling water or very high temperatures of 500°-600° C. In addition to their properties, these polymers are particularly adapted for use as high temperature materials and in applications such applications as carbon composites because of their stability in aggressive environments. For certain applications, such as antistatic devices, conductivity as low as about $10^{-8}$ s/cm might be suitable. Conductivity of about $10^{-8}$ s/cm marks the approximate threshhold of semiconducting materials which are believed to have conductivity range of up to about $10^3$ s/cm.

What I claim:

1. A substance selected from substituted and unsubstituted monomers and polymers of said monomers, said monomers having the following structure:

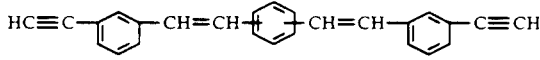

wherein in the substituted monomers, at least one hydrogen thereof is substituted with a substituent selected from the group consisting of phenyl groups, halogens, alkyl groups, nitro groups, alkoxy groups, phenoxy groups, ether groups, and mixtures thereof.

2. Substance of claim 1 wherein the middle benzene ring is bonded at 1 and 3 positions on the ring.

3. Substance of claim 1 wherein the middle benzene ring is bonded at 1 and 4 positions on the ring and wherein in the substituted substance at least one hydrogen is substituted with a substituent selected from fluorine, chlorine, bromine, alkyl groups containing 1-6 carbon atoms, alkoxy groups containing 1-6 carbon atoms, phenoxy groups containing 6-9 carbon atoms, and ether groups containing 1-6 carbon atoms.

4. Substance of claim 1 which is a thermoplastic polymer.

5. Substance of claim 1 which is a thermosetting polymer, is insoluble in solvents, and is electrically conducting.

6. Substance of claim 5 which has no acetylene groups, as determined by infrared analysis; and has conductivity of from $10^{-10}$ to at least about $10^2$ s/cm which remains substantially constant after said polymer is exposed to boiling water for 1000 hours.

7. Substance of claim 1 wherein at least one hydrogen thereon is substituted with a substituent selected from fluorine, chlorine, bromine and alkyl groups of 1-6 carbon atoms.

8. Substance of claim 1 wherein said substituent is selected from fluorine, chlorine, bromine, alkyl groups containing 1-6 carbon atoms, alkoxy groups 1-6 carbon atoms, phenoxy groups containing 6-9 carbon atoms, and ether groups containing 1-6 carbon atoms.

9. Substance of claim 1 wherein at least one hydrogen on one of said benzene rings is substituted with a substituent selected from fluorine, chlorine, bromine, alkyl groups containing 1-6 atoms, alkoxy groups containing 1-6 carbon atoms, phenoxy groups containing 6-9 carbon atoms, and ether groups containing 1-6 carbon atoms.

10. Process of preparing a substituted or unsubstituted polymer containing repeating units from the monomer having the following structure:

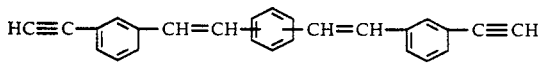

wherein in the substituted polymer, at least one hydrogen thereon is substituted with a substituent selected from the group consisting of phenyl groups, halogens, alkyl groups, nitro groups, alkoxy groups, phenoxy groups, ether groups, and mixtures thereof; the process comprising the step of heating said monomer at a temperature above its melting point until at least there is an increase in viscosity.

11. Process of claim 10 wherein the middle benzene ring is bonded at 1 and 3 positions on the ring and wherein in the substituted polymer at least one hydrogen thereon is substituted with a substituent selected from fluorine, chlorine, bromine, alkyl groups containing 1-6 atoms, alkoxy groups containing 1-6 carbon atoms, phenoxy groups containing 6-9 carbon atoms, and ether groups containing 1-6 carbon atoms.

12. Process of claim 10 wherein the middle benzene ring is bonded at 1 and 4 positions on the ring and wherein in the substituted polymer at least one hydrogen thereon is substituted with a substituent selected from fluorine, chlorine, bromine, alkyl groups containing 1-6 atoms, alkoxy groups containing 1-6 carbon atoms, phenoxy groups containing 6-9 carbon atoms, and ether groups containing 1-6 carbon atoms.

13. Process of claim 10 wherein said heating step is conducted at a temperature up to about 300° C. for a period of up to 10 hours, the resulting product being a thermoset polymer substantially devoid of acetylene absorption, as determined by infrared analysis.

14. Process of claim 10 wherein said heating step is conducted at a temperature of 120° to 160° C. for a period of time of 0.1 to 20 hours to produce a B-stage thermoplastic polymer.

15. Process of claim 10 wherein said heating step is conducted at a temperature of up to 300° C. for a period of up to 5 hours in order to obtain a thermosetting polymer.

16. Process of claim 15 including the step of heat treatment at an elevated temperature in excess of about 400° C. to develop electrical conductivity and environmental stability of said polymer.

17. Process of claim 16 wherein said heat treatment is conducted for a time sufficient to develop electrical conductivity from $10^{-10}$ to $10^2$ s/cm.

18. Process of claim 17 wherein said heat treatment is conducted at 400°-1200° C. for duration of 1-500 hours.

19. Process of claim 17 wherein said heat treatment is conducted at 500°-700° C. for duration of 5-200 hours.

20. Process of claim 17 wherein polymer conductivity remains substantially constant on exposure of said polymer to boiling water for 1000 hours.

* * * * *